United States Patent [19]
Aguadisch et al.

[11] Patent Number: 5,958,317
[45] Date of Patent: Sep. 28, 1999

[54] METHOD FOR MANUFACTURING A CONTROLLED-RELEASE DEVICE

[75] Inventors: Louis Michele Jacques Aguadisch; Andre Rudolf Louis Colas, both of Valbonne, France

[73] Assignee: Dow Corning France S.A., South Glamorgan

[21] Appl. No.: 08/912,428

[22] Filed: Aug. 18, 1997

[30] Foreign Application Priority Data

Aug. 14, 1996 [FR] France .................................... 96 10203

[51] Int. Cl.[6] .................................................. B29C 45/14
[52] U.S. Cl. ........................ 264/159; 264/255; 264/267; 264/251
[58] Field of Search .................................... 264/159, 267, 264/255, 294, 251, 1.24, 167, DIG. 37; 424/422, 438; 53/467

[56] References Cited

U.S. PATENT DOCUMENTS

| | | |
|---|---|---|
| 3,127,363 | 3/1964 | Nitzsche et al. |
| 3,161,614 | 12/1964 | Brown et al. |
| 3,479,422 | 11/1969 | Zavasnik .................................. 264/167 |
| 4,753,719 | 6/1988 | Yamaguchi et al. ..................... 264/255 |
| 5,788,977 | 8/1998 | Aguadisch et al. ..................... 424/422 |

FOREIGN PATENT DOCUMENTS

| | | |
|---|---|---|
| 465 744 | 1/1992 | European Pat. Off. . |
| 425 154 | 9/1993 | European Pat. Off. . |
| 962 061 | 10/1992 | United Kingdom . |

OTHER PUBLICATIONS

R. Meals, "Silicones," Encycl. Chem. Techn., 18, J. Wiley (N.Y., 1969).
I.D. Crossan, J. Appl. Polym. Symposium, 32, 421 (1977).

*Primary Examiner*—Jan H. Silbaugh
*Assistant Examiner*—Edmund H. Lee
*Attorney, Agent, or Firm*—Richard I. Gearhart

[57] ABSTRACT

A method of manufacturing a controlled-release device is described. The method comprises taking a hollow tubular element which is permeable to the active substance to be released and injecting it with at least two plugs of hardenable material. These plugs form partitions which block the hollow tubular element and are spaced apart to form at least one discrete hollow chamber. The hardenable material is then hardened and an active substance is introduced into at least one of the discrete hollow chambers.

10 Claims, 1 Drawing Sheet

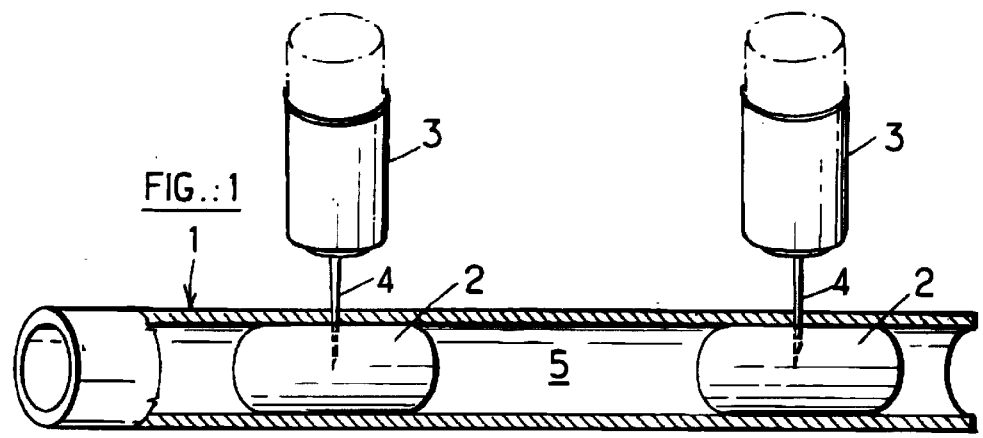
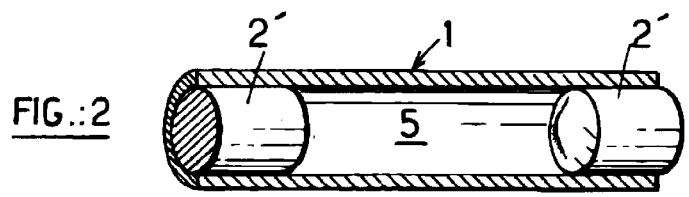
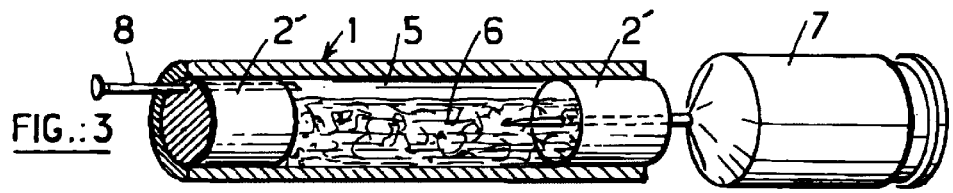
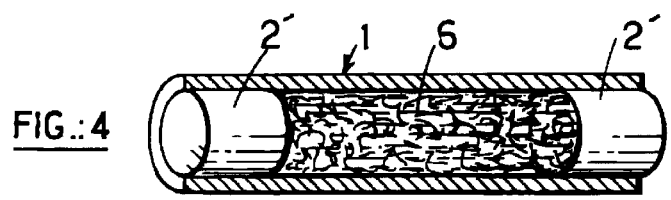
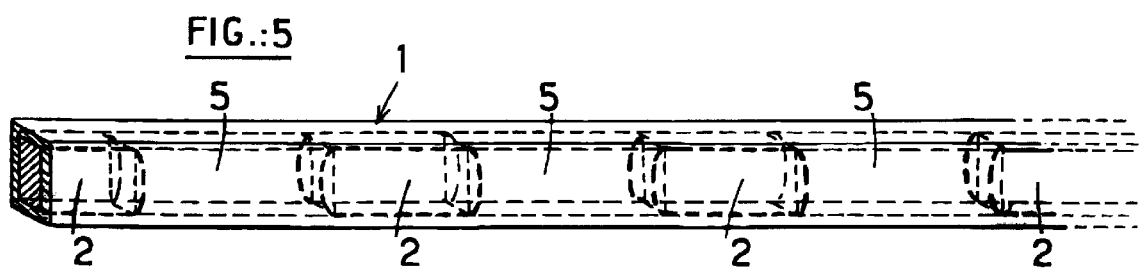

METHOD FOR MANUFACTURING A CONTROLLED-RELEASE DEVICE

The present invention relates to a method for manufacturing controlled-release devices.

Numerous devices have been proposed for the controlled release of drugs into the human or animal organism. For example, it has been proposed to manufacture a controlled-release drug administration device by using a vulcanized silicone elastomer tube, stopping one end with a vulcanizable silicone composition, filling the tube with a composition containing the drug, stopping the open end of the tube with a vulcanizable silicone composition, and then crosslinking the composition.

Although the devices manufactured in this way are efficacious as drug administration systems, their manufacture involves considerable time and effort because it requires several steps and a prolonged vulcanization time. Moreover the vulcanization reaction necessary to crosslink the silicone is generally hydrosilylation and this reaction can be impaired or greatly inhibited in the presence of certain chemical groups in certain drugs. This delay in vulcanization can be prevented by additional heating, but this is often not possible because the medicinal substances may be adversely affected by heating at temperatures greater than about 25° C.

It has now been found that one can easily produce devices for the delivery of active substance by using a hollow tubular element which is initially self-supporting (for example due to the thickness of the walls of the tube or due to the nature of the material constituting it), introducing plugs of vulcanizable material, and crosslinking the vulcanizable material to form partitions in the tube.

SUMMARY OF THE INVENTION

According to one of its aspects, the present invention provides a method for manufacturing a controlled-release device. The method comprises providing a hollow tubular element which is permeable to an active substance. At least two plugs of hardenable material are then injected into the hollow tubular element. These plugs form partitions which block the hollow tubular element and are spaced apart to form one or more chambers. The hardenable material is then hardened to form hardened plugs. Finally, an active substance is introduced into at least one of the chambers.

BRIEF DESCRIPTION OF THE DRAWINGS

FIGS. 1 to 4 are schematic partially broken-open views illustrating the manufacture of a device according to the invention and the device obtained in this way.

FIG. 5 illustrates another device according to the invention.

DETAILED DESCRIPTION OF THE INVENTION

The hollow tubular elements used herein can be formed by conventional techniques, such as extrusion at ambient temperature or at elevated temperature. The composition making up the hollow tubular element can be formulated in such a way that, in use of the device, it allows transfer of the active substance to the exterior of the device by, for example, diffusion, micropores or osmosis. Thus one may use a material which is inherently permeable to body fluids or a material which is not. The composition may be a material which hardens by vulcanizing after shaping or which is solidified simply on cooling.

The materials used to make the hollow tubular element can comprise any which are recognized as suitable for introduction or implantation in the human or animal body or compatible with an ecosystem. These include, for example, polymers and copolymers of unsaturated monomers such as polymethacrylates, polyvinyl chloride, polyethylene, polypropylene, polyacrylonitrile, polyvinyl acetate, polybutadiene, polyesters, polyamides, polyurethanes, cellulose esters and silicones.

The silicone-based materials commonly used for controlled-release drug administration devices are preferred herein. These are preferably hardenable materials which can be shaped and are capable of maintaining their shape, that is, of resisting flow after shaping and before crosslinking is fully developed. Also useful are composite materials including a silicone elastomer and a hydrophilic component, for example those described in EP-A-0 425 154 and EP-A-0 465 744.

The tubes preferred within the scope of this invention are silicone elastomer tubes obtained by extrusion or injection of silicone polymer compositions. Such tubes are available commercially. The silicone polymer compositions used to manufacture such tubes are also well known and described for example in R. Meals, "Silicones", Encycl. Chem. Techn., 18, J. Wiley (N.Y., 1969) or W. Lynch, "Handbook of Silicone Rubber Fabrication", Van Nostrand (N.Y., 1978). These are heat-hardenable compositions, the crosslinking of which is provided by an addition reaction catalyzed with a platinum complex or by initiation with peroxides. Generally these compounds contain a reinforcing filler such as pyrogenous silica, as well as the additives necessary for crosslinking.

The compositions used to plug the hollow tubular element herein are generally selected from the same or similar materials used to form the hollow tubular element. The materials used to form the hollow tubular element and the hardenable, plugging material may, however, be identical or different.

The plugging compositions are characterized by their limited flow as defined by the ASTM D-2202 or Mil-S 8802 test. Such materials do not significantly flow under the effect of their own weight (fluids with flow threshold) or they have high enough viscosity so that hardening thereof (by vulcanization or simple solidification) occurs before significant flow occurs. The plugging materials are also characterized by their capacity to crosslink to an elastomer and to adhere to the inner surface of the tubular element.

The preferred plugging compositions are silicone elastomers of the mono or bicomponent type. Such compositions are capable of cold or hot crosslinking by, for example, a condensation or an addition reaction. Such compositions are well known and described, for example, in R. Meals, "Silicones", Encycl. Chem. Techn., 18, J. Wiley (N.Y., 1969) or in I.D. Crossan, J. Appl. Polym. Symposium, 32, 421 (1977). These compositions are viscous but, nevertheless, can be pumped or injected at low pressure because of their thixotropic nature. Generally they contain a reinforcing filler such as pyrogenous silica as well as the additives necessary for crosslinking. Flow in such compositions is limited by the presence of mineral filler, additive and/or polymer of high viscosity. The adhesion of such compositions may be improved by adding substances such as silanes, titanates or other substances which may promote adhesion. Crosslinking can be accomplished by several systems or reactions such as the use of silanes with alkoxy, acetoxy, aminoxy functionality or oligomers with SiH functionality or catalysts derived from tin or platinum.

The silicone-based composition constituting the tubular element and/or the plugs preferably includes an organosilicon compound which can be used in the form of a hot melted mass or, more preferably, capable of undergoing crosslinking in the presence or absence of crosslinking agent so as to be hardenable in a state preserving its shape and, preferably, elastomeric. This crosslinking may be performed at ambient temperatures or at elevated temperatures, preferably on the order of up to 210° C.

Elastomer-forming organosilicon compounds which may be used include polyorganosiloxanes having silicon-bound hydroxyl groups which may be crosslinked into elastomers by adding a crosslinking agent and a condensation catalyst. In these compounds, the polyorganosiloxane is generally a polydiorganosiloxane having terminal silanol groups. The crosslinking agent may be, for example, an alkoxysilane or a polyalkylsilicate, for example methyl trimethoxysilane or a polyethylsilicate, or a polyalkylhydrosiloxane may be involved, for example a polymethylhydrosiloxane. Various catalysts can be used and representative examples include organometal compounds such as stannous octoate, dibutyltin dilaurate, alkyltitanates and titanium chelates. These elastomer-forming compounds are well known in the art and they have been described, for example, in British patents numbers 841 825, 957 255 and 962 061.

Preferred elastomer forming silicone compositions are those which are crosslinked, for example by heating, without producing volatile by-products. Among the advantages offered by using the preferred materials, the absence of volatile by-products ensures the absence of undesirable voids in the molded product and makes it possible to use a simple method of manufacture. Compositions which are crosslinked by a radical mechanism when they are irradiated or heated or thermoplastic compositions may be used.

The most preferred compositions are silicone compositions which are crosslinked by a hydrosilylation reaction. These include one or more polyorganosiloxanes having at least two silicon-bound aliphatically unsaturated groups per molecule, one or more organosilicon compounds having at least two silicon-bound hydrogen atoms and a catalyst which activates the reaction between the unsaturated groups and the silicon-bound hydrogen atoms such as a precious metal catalyst, e.g., a platinum compound or complex. The aliphatically unsaturated groups are preferably olefinically unsaturated.

The polyorganosiloxane used in this most preferred composition is typically a high molecular weight polysiloxane and includes units of the general formula $Q_aQ'SiO_{(3-a)/2}$ and $Q_bSiO_{(4-b)/2}$ where Q denotes a monovalent hydrocarbon or substituted hydrocarbon group having not more than 8 carbon atoms, for example a methyl group or a phenyl group, Q' denotes an organic group having olefinic unsaturation, preferably a vinyl, allyl or hexenyl group, at least 80% of the other silicon-bound substituents being methyl groups, the value of a is 1 or 2 and the value of b is 0, 1, 2 or 3.

The organosilicon compound used in this most preferred composition is typically an organohydrosiloxane having a viscosity of about 50 mm$^2$/s and having at least two silicon-bound hydrogen atoms per molecule, the other silicon-bound substituents being monovalent hydrocarbon groups having not more than 8 carbon atoms, preferably methyl groups.

The platinum-containing compound or complex used in this most preferred composition may be, for example, chloroplatinic acid, platinum acetonyl acetonate or a complex of platinum halides with unsaturated compounds such as ethylene, propylene, organovinylsiloxanes or styrene.

The composition optionally and preferably includes a catalyst inhibitor, for example an alkynyl compound such as an acetylenically unsaturated secondary or tertiary alcohol, for example ethynylcyclohexanol.

The preferred compositions include a silicone composition formulated so as to offer a "working time" sufficient to allow execution of the shaping method and capable of effecting complete vulcanization with elimination of volatile materials by heating, preferably at a temperature within the range up to 200° C. Compositions of this type are well known in technology and are commercially available.

The composition may and preferably does include a finely divided filler. For example, the composition normally contains one or more finely divided reinforcing or diluting fillers such as precipitated or pyrogenous silicas with high specific surface area, crushed quartz, diatomaceous earths, calcium carbonate, barium sulfate, iron oxide, titanium dioxide and carbon black. The proportion of these fillers used depends on the desired properties for the elastomer-forming composition and for the hardened elastomer. Usually the filler content of the composition is within the range from about 5 to about 100 parts by weight per 100 parts by weight of polymer.

The expression "active substance" is used herein to designate agents which are essential to the life of living organisms, those which contribute to maintaining the life or nutrition of living organisms, in particular therapeutic or diagnostic agents which can be used in the treatment of the human or animal organism, substances which improve the quality of life such as cosmetic or deodorant agents (odoriferous principles, fragrances, perfumes) or substances acting on an ecosystem. Examples of these substances include those which are designed to be released by diffusion, permeation or osmosis into the body fluids, as well as in contact with a human or animal body or the ecosystem. They may involve organic or mineral or hydrophilic or lipophilic substances. These substances may be pharmaceutically active, have a beneficial action on the ecosystem, or merely cosmetic. They also may be substances for which it is useful to administer, for example, over a long period of time.

The active substance may be chosen according to normal pharmaceutical, veterinary, cosmetic, agronomic or other practice and its pH is normally adapted to the conditions prevailing in the region where it is to be released. If occasion arises, the pH of the substance may be buffered in order to preserve the activity of the substance. Therapeutic agents which may be used include, for example, organic and mineral drugs which act on the central nervous system, contraceptive drugs, hormone supplements, cardiovascular and ophthalmic drugs and antiparasitic, antifungal and antiviral agents.

According to the method of the invention, at least 2 plugs of the above plugging compositions are injected into the hollow tubular element. Each of the plugs are injected in a manner so as to form a partition which blocks the hollow tubular element. The plugs are also spaced apart from each other so as to define one or more discrete chambers within the hollow tubular element. The length of each plug may be from a few millimeters to a few centimeters.

Next, the plugging compositions are hardened. This may be accomplished by the means described above depending on, for example, the plugging composition. Advantageously, the plugs or partitions, after crosslinking, allow the introduction of an active material into the chamber by injection through said plugs or partitions, for example by means of a hypodermic needle or the like, said material being capable of self-healing, that is, of closing up by itself on withdrawal of the needle.

The active substance is then introduced into at least one of the chambers. This may be accomplished in any practical way desired. Preferably, however, the active substance is also injected, for example with the aid of a syringe, through one of the plugs limiting the chamber. Advantageously an air outlet is also provided, for example by piercing with a hollow needle through the other plug limiting the chamber.

The active substance will usually be introduced in liquid form, for example in the form of a solution or dispersion in water or in a suitable solvent. It is also possible to inject a liquid active substance into the hollow chamber and then form a material of a solid nature or high viscosity, for example, by cooling, crosslinking or other forms of solidification. A similar approach is possible if the injected substance is thixotropic. In such a case, it is not necessary to inject the active substance through a partition which closes up by itself. A powdered active substance may be dispersed in a volatile solvent, for example, a silicone or other which allows for its introduction into the chamber. Evaporation of the solvent leaves a powdered deposit in the chamber. In another embodiment, a slit is formed in the tubular element, through which the active substance can be introduced into the interior of said tubular element, for example in the form of a powder or solid.

The concentration of active substance used, the volume of the device and the thickness of its casing are chosen so as to offer the required rate of release of the active substance or substances and the required working life of the device, that is, the time during which the device is capable of releasing the active substance at the required rate.

The method of the invention makes it possible to produce controlled-release devices of various shapes or configurations and in particular devices of the reservoir type. The hollow tubular element can have a circular, rectangular or other cross-section. The tubular element divided into multiple discrete chambers can be cut into cylindrical devices comprising just one or more chambers. A divided tubular element can also be curved and connected at its ends to form a ring or collar. In the devices comprising two or more chambers, different active substances can be introduced into each chamber, if desired.

By using a method according to the invention it is possible to manufacture a casing of hardened material which can be sterilized and from which all volatile materials have been eliminated before the active substance is introduced into it. Thus, an active substance can be introduced without any fear of it being adversely affected by heating in a subsequent production step or of it being able to hinder the reaction of crosslinking the silicone network.

The following description and attached drawings will allow an understanding of the invention.

FIGS. 1 to 4 are schematic partially broken-open views illustrating the manufacture of a device according to the invention and the device obtained in this way; and FIG. 5 illustrates another device according to the invention.

To manufacture a device according to the invention, one can start with a preformed tube, for example a medical tube of silicone elastomer commercially available under the registered trademark Silastic® RX50 having a hardness on the Shore A scale of 50 (product sold by the company DOW CORNING CORPORATION). This tube has an outside diameter of 17.46 mm, an inside diameter of 12.70 mm and a wall thickness of 2.38 mm.

The silicone composition used for the manufacture of this Silastic RX50 tube is a typical silicone elastomer. This composition contains high molecular weight silicone polymers carrying vinyl reactive groups, a crosslinking agent containing SiH reactive groups, a reinforcing pyrogenous silica filler and a platinum complex for catalyzing the reaction of crosslinking by addition. Owing to its consistency before crosslinking, this silicone composition is particularly designed for the manufacture of tubes by extrusion and crosslinking at elevated temperature.

As FIG. 1 shows, spaced-apart plugs 2 are formed in the preformed tube 1 by injecting medical adhesive Silastic® of type A into the tube with the aid of a pneumatic syringe 3 provided with a needle 4 by piercing the wall of the tube 1.

Silastic A is a silicone adhesive of the monocomponent type which is vulcanizable at ambient temperature in the presence of humidity. It is characterized by high extrudability which allows for its injection but also by its limited flow after injection. It is a thixotropic product, which thixotropy arises from the presence of a reinforcing pyrogenous silica. The adhesive also contains the elements necessary for crosslinking it at ambient temperature in the presence of humidity and its formulation allows excellent adhesion to the inner surface of the tubular element.

Successive injections in the tube 1 are done at intervals of 80 mm. The injected adhesive flows substantially symmetrically on either side of the injection point. A sufficient quantity of the adhesive is injected at each site to obstruct the light of the tube 1, while leaving an empty volume or empty chamber 5 free from adhesive between two successive plugs.

The injected plugs are then allowed to vulcanite under the action of the ambient humidity until they adhere well to the tube.

The tube is then cut into sections, performing each cut substantially in the middle of the vulcanized plugs. Thus a tubular receptacle blocked at both ends by plugs 2' is obtained, as illustrated by FIG. 2. This receptacle is then filled with any desired active substance 6, for example by injecting the latter into the chamber 5 with the aid of a syringe with needle 7 and through one of the end plugs 2'. Advantageously, a needle 8 is passed through the other end plug 2' to allow evacuation of air as the chamber 5 is filled with the active material, as FIG. 3 illustrates.

After filling and removing the needles, the delivery device illustrated in FIG. 4 is obtained. As the vulcanized silicone adhesive forming the plugs 2 has self-healing properties, the holes made by the needles in the plugs 2' close by themselves.

FIG. 5 illustrates another device according to the invention.

This device is in the form of a string of rectangular sections including a succession of hollow portions (chambers) and solid portions (plugs). Production in a first step is based on extrusion of the hollow rectangular profile. The profile is made by extruding a Silastic® Q7-4780 ETR silicone elastomer through a rectangular outer die with a width of 14.80 mm and a height of 6.10 mm, provided with a rectangular punch with a width of 12.15 mm and a height of 3.00 mm. The profile is crosslinked by passage through an oven maintained at 180° C. The resultant tube has a rectangular cross section with a width of 15.25 mm, a height of 6.31 mm and a thickness of 1.73 mm. The tube is then sequentially blocked by injection of Silastic® type A medical adhesive using a pneumatic syringe provided with a needle allowing piercing of the tube wall and injection of the adhesive plug, as described with respect to FIGS. 1–4. The latter flows symmetrically on either side of the injection point, producing obstruction of the light of the tube. Monitoring the production of the hollow and plugged sequences can be done visually. The profile is maintained at ambient temperature to allow crosslinking of the adhesive plugs 2. Filling with active substance can be performed through the self-sealing plugs, one needle allowing filling, another degassing. One or more of the chambers can be filled.

Such a string may be useful, for example, for producing antiparasitic collars for dogs or cats, given that it is appropriate to provide at the ends of the string a system (not shown) making it possible to fix these ends together.

Naturally the string of FIG. 5 could also be cut into single-chamber receptacles of the type shown in FIG. 2. Such a single-chamber receptacle has been filled with melted menthol, thus producing a device delivering menthol vapors at a constant rate of 2.5% by weight per day over 40 days.

It goes without saying that the embodiments described are only examples and they could be modified, particularly by substituting technical equivalents, without departing from the scope of the invention.

That which is claimed is:

1. A method for manufacturing a controlled-release device comprising:
   (i) providing a preformed hollow tubular element having a wall, said hollow tubular element being permeable to an active substance,
   (ii) injecting at least two plugs of hardenable material into the preformed tubular element through the wall, said plugs forming partitions within the space defined by the wall of the hollow tubular element and said plugs being spaced apart so as to form one or more chambers,
   (iii) hardening the hardenable materials to form hardened plugs, and
   (iv) introducing the active substance into at least one of the said chambers.

2. The method of claim 1 wherein the controlled-release device resulting from step (iii) is cut into sections by cutting transversely through an area of the article that comprises the hollow tubular element and hardened plugs to result in a section of the hollow tubular element plugged at both ends with hardened plugs and incorporating at least one chamber therebetween.

3. The method of claim 1 wherein the controlled-release device resulting from step (iv) is cut into sections by cutting transversely through an area of the article that comprises the hollow tubular element and hardened plugs to result in a section of the hollow tubular element plugged at both ends with hardened plugs and incorporating at least one chamber therebetween which contains the active substance.

4. The method according to claim 1 wherein the hollow tubular element and the hardened plugs are silicone-based materials.

5. The method according to claim 4 wherein the material which constitutes the preformed hollow tubular element further contains a hydrophilic component.

6. The method according to claim 1 wherein the active substance is introduced into the chamber in liquid form by injection through a needle which is pierced through one of the hardened plugs.

7. The method according to claim 1 wherein the material which constitutes the hardened plugs exhibits self-healing properties.

8. The method according to claim 1 wherein at least three plugs of hardenable material are injected into the preformed hollow tubular element so as to form at least two chambers in a string.

9. The method according to claim 1 wherein the active substance is therapeutic for a human or animal body.

10. The method according to claim 1 wherein the active substance is selected from the group consisting of cosmetics and deodorants.

* * * * *